United States Patent [19]

Varma et al.

[11] Patent Number: 4,528,138

[45] Date of Patent: Jul. 9, 1985

[54] 16-KETO-17-SUBSTITUTED THIA-17-ALKYL(OR ALKENYL OR ALKYNYL) ANDROSTENES

[75] Inventors: Ravi K. Varma, Belle Mead; Donald S. Karanewsky, East Windsor, both of N.J.

[73] Assignee: E. R. Squibb & Sons, Inc., Princeton, N.J.

[21] Appl. No.: 622,509

[22] Filed: Jun. 20, 1984

[51] Int. Cl.³ .................................................. C07J 1/00
[52] U.S. Cl. .................................................. 260/397.45
[58] Field of Search .................................... 260/397.45

[56] References Cited

U.S. PATENT DOCUMENTS

| | | | |
|---|---|---|---|
| 4,091,036 | 5/1979 | Varma | 260/397.45 |
| 4,094,840 | 6/1978 | Varma | 260/397.45 |
| 4,133,811 | 1/1979 | Varma | 260/397.45 |
| 4,146,538 | 3/1979 | Varma et al. | 260/397.45 |
| 4,252,733 | 2/1981 | Varma | 260/397.45 |
| 4,265,815 | 5/1981 | Varma | 260/397.45 |
| 4,361,559 | 11/1982 | Varma | 424/243 |
| 4,420,428 | 12/1983 | Varma | 260/397.45 |
| 4,427,592 | 1/1984 | Varma et al. | 260/397.45 |
| 4,447,426 | 5/1984 | Wang et al. | 260/397.45 |

Primary Examiner—Elbert L. Roberts
Attorney, Agent, or Firm—Lawrence S. Levinson; Donald J. Barrack

[57] ABSTRACT

Antiinflammatory activity is exhibited by steroids having the formula

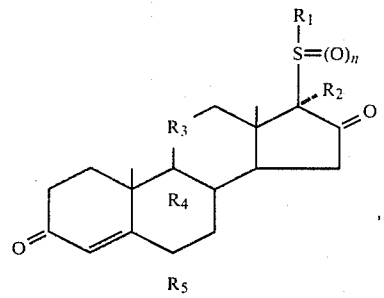

and the 1,2-dehydro derivative thereof, wherein
$R_1$ is alkyl, mono-, di- or trifluoroalkyl,

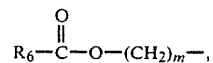

aryl or alkylthioalkyl, wherein $R_6$ is alkyl or aryl and m is 1, 2, 3 or 4;
$R_2$ is

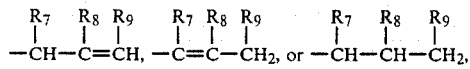

wherein $R_7$, $R_8$ and $R_9$ are each independently hydrogen or alkyl of 1 to 4 carbon atoms;
$R_3$ is carbonyl or $\beta$-hydroxymethylene;
$R_4$ is hydrogen or halogen;
$R_5$ is hydrogen, methyl or fluorine; and
n is 0, 1 or 2;
with the proviso that if $R_1$ is alkylthioalkyl, n is 0.

12 Claims, No Drawings

16-KETO-17-SUBSTITUTED THIA-17-ALKYL(OR ALKENYL OR ALKYNYL) ANDROSTENES

RELATED APPLICATIONS

U.S. patent application Ser. No. 576,668, filed Feb. 3, 1984, discloses (as antiinflammatory agents) androstenes having the partial structural formula

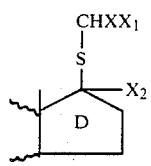

wherein X is hydrogen, alkyl or aryl; $X_1$ is hydrogen, alkyl,

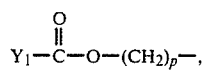

alkylthio, alkoxy, fluoro, hydroxyalkyl, cyanoalkyl, alkoxycarbonyl—$(CH_2)_p$—, mono-, di- or trifluoroalkyl, or

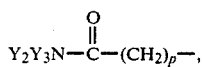

wherein p is 0, 1, 2, 3 or 4, $Y_1$ is alkyl or aryl, and $Y_2$ and $Y_3$ are the same or different and each is hydrogen or alkyl; and $X_2$ is alkyl, alkenyl or alkynyl.

BACKGROUND OF THE INVENTION

U.S. Pat. No. 4,361,559, issued Nov. 30, 1982, discloses (as antiinflammatory agents) 3-ketoandrostenes having in the 17-position the substituents $A_1$—S— and $A_2$—S— wherein $A_1$ and $A_2$ are the same or different and each is alkyl, cycloalkyl or aryl.

U.S. Pat. No. 4,094,840, issued June 13, 1978, discloses (as antiinflammatory agents) androstenes having the partial structural formula

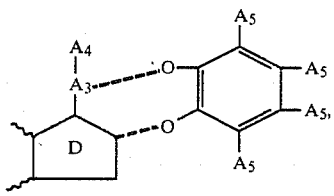

wherein $A_3$ is —, S—

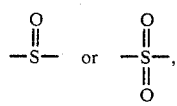

$A_4$ is alkyl, aryl, acyloxyalkyl, and the $A_5$ groups are halogen.

U.S. Pat. No. 4,091,036, issued May 23, 1978, discloses (as antiinflammatory agents) androstenes having the partial structural formula

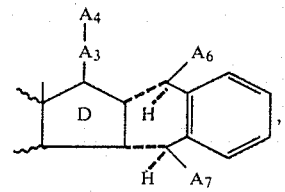

wherein $A_3$ and $A_4$ are as defined above, and $A_6$ and $A_7$ are the same or different and are hydrogen, alkyl, alkoxy, carboalkoxy, formyl,

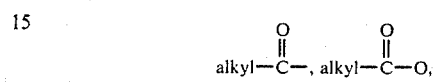

hydroxy, halogen, phenyl or cyano, with the proviso that when $A_6$ and $A_7$ are different, one of $A_6$ and $A_7$ is hydrogen.

U.S. Pat. No. 4,146,538, issued Mar. 27, 1979, discloses (as antiinflammatory agents) androstenes having the partial structural formula

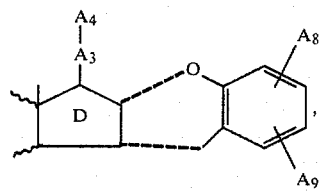

wherein $A_3$ and $A_4$ are as defined above, and $A_8$ and $A_9$ are the same or different and are hydrogen, halogen, alkyl, or alkoxy, or $A_8$ and $A_9$ together with the benzene ring to which they are attached form a naphthalene group.

U.S. Pat. No. 4,265,815, issued May 5, 1981 discloses (as chemical intermediates) androstenes having the partial structural formula

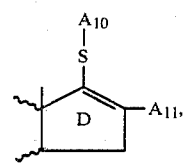

wherein $A_{10}$ is alkyl, aryl, arylalkyl or acyloxyalkyl and $A_{11}$ is chloro, bromo, alkoxy, aryloxy, alkylthio or arylthio.

U.S. Pat. No. 4,252,733, issued Feb. 24, 1981, discloses (as antiinflammatory agents) androstenes having the partial structural formula

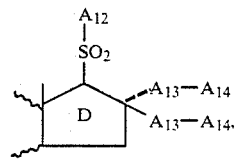

wherein $A_{12}$ is alkyl or aryl, $A_{13}$ is oxygen or sulfur and $A_{14}$ is alkyl or arylalkyl, or together the $A_{14}$ groups are —$(CH_2)$—$_{2\ or\ 3}$.

U.S. Pat. No. 4,420,428, issued Dec. 13, 1983 discloses (as antiinflammatory agents) androstenes having the partial structural formula

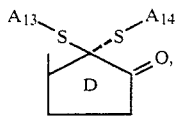

wherein $A_{13}$ and $A_{14}$ are the same or different and each is alkyl, cycloalkyl or aryl.

U.S. Pat. No. 4,427,592, issued Jan. 24, 1984, discloses (as antiinflammatory agents) androstenes having the partial structural formula

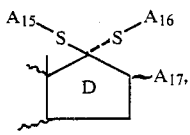

wherein one of $A_{15}$ and $A_{16}$ is alkyl, aryl, arylalkyl, or cycloalkyl, and the other is alkenyl, substituted alkenyl, alkynyl, substituted alkynyl, mono-, di- or trifluoroalkyl, cyanoalkyl, alkanoylalkyl or $$-(CH_2)_p-\overset{O}{\underset{\|}{C}}-NY_4Y_5$$

wherein p is 1, 2, 3 or 4 and $Y_4$ and $Y_5$ are the same or different and each is hydrogen or alkyl, and $A_{17}$ is hydrogen, hydroxy, alkoxy, aryloxy, oxo, methylene, alkylthio, arylthio, alkanoyl, alkanoyloxy or fluorine.

U.S. Pat. No. 4,447,426, issued May 8, 1984, discloses (as antiinflammatory agents) androstenes having the partial structural formula

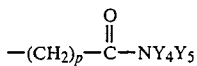

wherein one of $A_{18}$ and $A_{19}$ is alkyl, cycloalkyl, aryl, arylalkyl, or —$CH_2X_3$ wherein $X_3$ is alkylthio, alkoxy, aroyloxy, alkanoyloxy or alkoxycarbonyl, and the other is alkylthioalkyl, alkoxyalkyl, alkanoyloxyalkyl, aroyloxyalkyl, alkoxycarbonylalkyl, carboxylalkyl or arylalkyl and $A_{20}$ is hydrogen, hydroxy, alkoxy, aryloxy, oxo, methylene, alkylthio, arylthio, alkanoyl, alkanoyloxy, or halogen.

SUMMARY OF THE INVENTION

Steroids having the formula

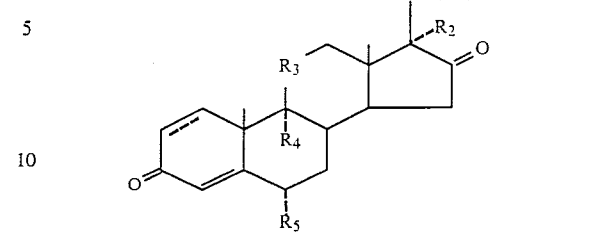

have antiinflammatory activity. In formula I, and throughout the specification, the symbols are as defined below.

$R_1$ is alkyl, mono-, di- or trifluoroalkyl, $$R_6-\overset{O}{\underset{\|}{C}}-O-(CH_2)_m-,$$

aryl or alkylthioalkyl, wherein $R_6$ is alkyl or aryl and m is 1, 2, 3 or 4;

$R_2$ is

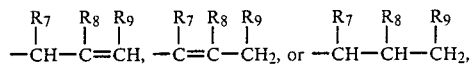

wherein $R_7$, $R_8$ and $R_9$ are each independently hydrogen of alkyl or 1 to 4 carbon atoms;
$R_3$ is carbonyl or β-hydroxymethylene;
$R_4$ is hydrogen or halogen;
$R_5$ is hydrogen, methyl or fluorine; and
n is 0, 1 or 2;
with the proviso that if $R_1$ is alkylthioalkyl, n is 0. The dotted line in the 1,2-position of the structural formulas shown in this specification indicate the optional presence of ethylenic unsaturation.

The term "aryl", are used throughout the specification either individually or as part of a larger group, refers to phenyl or phenyl substituted with one, two or three alkyl, alkoxy or halogen groups.

The term "halogen", as used throughout the specification either individually or as part of a larger group, refers to fluorine, chlorine, bromine and iodine.

The terms "alkyl" and "alkoxy", as used throughout the specification either individually or as part of a larger group, refer to groups having 1 to 12 carbon atoms.

DETAILED DESCRIPTION OF THE INVENTION

The steroids of formula I, and the 1,2-dehydro and 6,7-dehydro derivatives thereof, are topical antiinflammatory agents that can be used to treat skin conditions such as dermatitis, psoriasis, sunburn, eczema, neurodermatitis, or anogenital pruritus, and inhalation therapy for topical treatment of allergy and asthma.

For the treatment of skin conditions, the topical antiinflammatory steroids of this invention may be administered in a conventional pharmaceutical carrier in the form of a cream, ointment, lotion or the like. The steroids will preferably be used in the range of 0.01 to 5.0% by weight of the vehicle, preferably 0.05 to 2.0% by weight of the vehicle.

For the topical treatment of allergy and asthma, the topical antiinflammatory steroids of this invention may be administered in the conventional manner, e.g., as solid medicament which has been atomized. U.S. Pat. Nos. 3,948,264 and 4,147,166 are exemplary of the literature which describes devices that can be used to administer solid medicaments for inhalation therapy.

The steroids of formula I can be prepared using the corresponding steroid having the formula

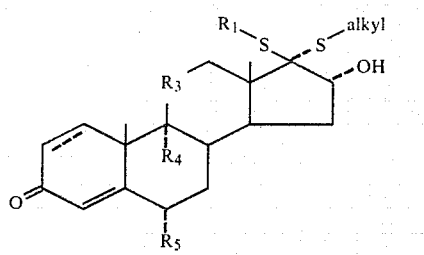

as a starting material. These steroids are disclosed in U.S. Pat. Nos. 4,361,559, issued Nov. 30, 1982, 4,427,592, issued Jan. 24, 1984, and 4,447,426, issued May 8, 1984.

Reaction of a steroid of formula II with a compound having the formula

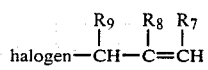

in the presence of an inorganic base (e.g., sodium hydride) yields the corresponding steroid having the formula

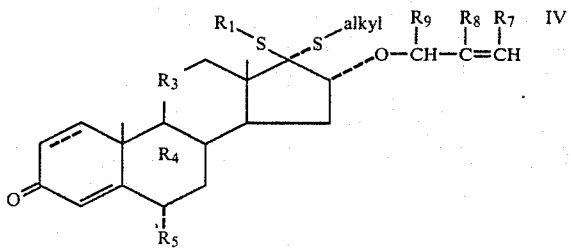

The steroids of formula IV are novel intermediates, and as such, form an integral part of this invention.

Thermolysis of an intermediate of formula IV, preferably in an aromatic solvent (e.g., diethylbenzene) yields the corresponding steroid product having the formula

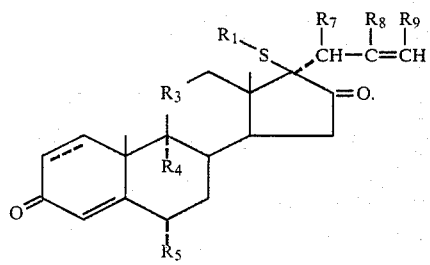

Treatment of a product of formula V with a transition metal catalyst (e.g., palladium on carbon or rhodium chloride) or an acid catalyst yields the isomeric product having the formula

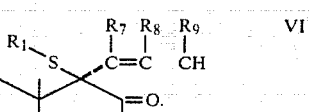

Hydrogenation of a product of formula V in the presence of a catalyst such as triphenylphosphine rhodium chloride yields the corresponding product having the formula

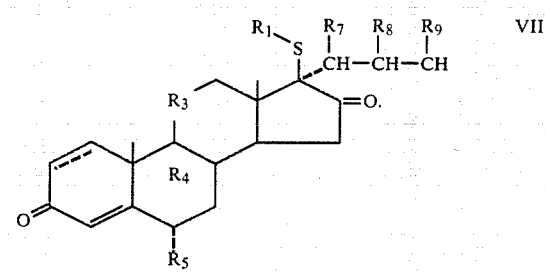

The sulfides of formula I (n is 0) can be oxidized to the corresponding sulfinyl steroids (products of formula I, n is 1) or sulfonyl steroids (products of formula I, n is 2) with peracids (e.g., m-chloroperoxybenzoic acid or periodic acid). The use of one equivalent of oxidizing agent will yield predominantly a sulfoxide and the use of two or more equivalents of oxidizing agent will yield predominantly a sulfone. The oxidation reaction can be run in an organic solvent, e.g., a halogenated hydrocarbon such as chloroform. Alternatively, the sulfonyl steroids of formula I can be prepared by oxidizing the corresponding sulfinyl steroid.

The following example is a specific embodiment of this invention.

EXAMPLE 1

(11β, 17β)-9-Fluoro-11-hydroxy-17-(methylthio)-17-(2-propenyl)androsta-1,4-dien-3,16-dione (A) (11β, 16α)-11-(Acetyloxy)-9-fluoro-17,17-bis-(methylthio)-16-(2-propenyloxy)androsta-1,4-dien-3,16-dione A solution of 11β-(acetyloxy)-9-fluoro-16α-hydroxy-17,17-bis(methylthio)androsta-1,4-dione-3-one (1.0 g, 2.2 mmole) in dry tetrahydrofuran (15.0 ml) was cooled in an ice bath and a 1.7M solution of n-butyl lithium in hexane (1.35 ml, 2.30 mmole) was added. After 5.0 minutes, dry dimethylformamide (5.0 ml) was added, followed by allyl bromide (1.0 ml). After 2.0 hours, tlc examination of an aliquot showed essentially complete absence of the starting steroid. The mixture was then added into water and extracted with chloroform. The extracts were combined, washed with water, dried (anhydrous magnesium sulfate) and evaporated to afford the crude product. This was subjected to a preparative tlc on four 2.0×200×200 mm silica gel plates (using chloroform-ethyl acetate (9:1) for development and chloroform-methanol (3:1) for extraction of the bands)

to isolate, in the order of increasing polarity, the following compounds: two minor components which were not characterized (95 mg), the title compound (630 mg), (11β,16α)-9-fluoro-11-hydroxy-17,17-bis(methylthio)-16-(2-propenyloxy)-androsta-1,4-dien-3-one (180 mg) and unreacted starting material (110 mg). The (11β,16α)-9-fluoro-11-hydroxy-17,17-bis(methylthio)-16-(2-propenyloxy)androsta-1,4-dien-3-one presumably resulted because of moisture present in the solvents. The title compound showed an $^1$H NMR spectrum consistent with the structure.

(B)

(11β,16α)-9-Fluoro-11-hydroxy-17,17-bis(methylthio)-16-(2-propenyloxy)androsta-1,4-dien-3-one A solution of (11β,16α)-11-(acetyloxy)-9-fluoro-17,17-bis(methylthio)-16-(2-propenyloxy)-androsta-1,4-dien-3,16-dione (594 mg, 1.2 mmole) in a mixture of methanol (15 ml) and tetrahydrofuran (15 ml) was stirred with 3M sodium hydroxide (2.0 ml) under an atmosphere of nitrogen for 1.0 hour. A slight excess of glacial acetic was then added and the mixture was concentrated in vacuo. The residue was diluted with water and extracted with chloroform. The chloroform extracts were combined, washed with water, dried (anhydrous magnesium sulfate), evaporated and mixed with the material (180 mg) isolated earlier (see part A) to afford a homogeneous (tlc) solid (700 mg). One crystallization of this from ethyl acetate and drying (110° C., 0.3 mm of Hg, 6.0 hours) afforded the analytical specimen of the title compound (520 mg) as heavy white prisms, melting point 226°–227° C. (dec.), with consistent spectral data.

Anal. Calc'd. for $C_{24}H_{33}FO_3S_2$: C, 63.68; H, 7.35; S, 14.17; F, 4.20; Found: C, 63.96; H, 7.52; S, 14.22; F, 4.32

(C)

(11β,17β)-9-Fluoro-11-hydroxy-17-(methylthio)-17-(2-propenyl)androsta-1,4-dien-3,16-dione A suspension of (11β,16α)-9-fluoro-11-hydroxy-17,17-bis(methylthio)-16-(2-propenyloxy)-androsta-1,4-diene-3-one (460 mg, 1.02 mmole) in distilled, dry diethylbenzene (20 ml) was refluxed under a drying tube. A solution resulted, which turned yellow in color. After less than one-half hour, examination of an aliquot of the solution by tlc showed the absence of the starting steroid. The solution was then cooled to room temperature and was filtered through a column of silica gel (10 g) using chloroform-hexane (1:1) for the filtration. This filtrate was discarded. Subsequent elution of the column with chloroform-ethyl acetate (9:1) followed by evaporation of the eluates furnished the title compound as a slightly contaminated solid (367 mg). This was once crystallized from ethyl acetate and dried (110° C., 0.3 mm of Hg, 6.0 hours) to afford the analytical specimen as white heavy prisms (238 mg), melting point 223°–224° C., with consistent spectra data.

Anal. Calc'd. for $C_{23}H_{29}FO_3S$: C, 68.29; H, 7.23; F, 4.70; S, 7.93; Found: C, 68.06; H, 7.18; F, 4.76; S, 7.88

What is claimed is:

1. A steroid having the formula

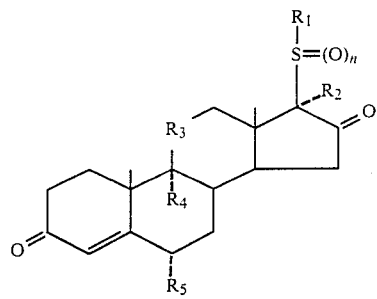

or a 1,2-dehydro derivative thereof, wherein $R_1$ is alkyl, mono-, di- or trifluoroalkyl,

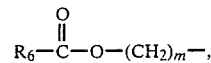

aryl or alkylthioalkyl, wherein $R_6$ is alkyl or aryl and m is 1, 2, 3 or 4;

$R_2$ is

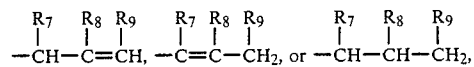

wherein $R_7$, $R_8$ and $R_9$ are each independently hydrogen or alkyl of 1 to 4 carbon atoms;

$R_3$ is carbonyl or β-hydroxymethylene;

$R_4$ is hydrogen or halogen;

$R_5$ is hydrogen, methyl or fluorine; and n is 0, 1 or 2;

with the proviso that if $R_1$ is alkylthioalkyl, n is 0.

2. A steroid in accordance with claim 1 wherein $R_1$ is alkyl.

3. A steroid in accordance with claim 1 wherein $R_1$ is mono-, di- or trifluoroalkyl.

4. A steroid in accordance with claim 1 wherein $R_1$ is

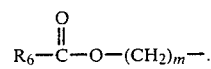

5. A steroid in accordance with claim 1 wherein $R_1$ is aryl.

6. A steroid in accordance with claim 1 wherein n is 0 and $R_1$ is alkylthioalkyl.

7. A steroid in accordance with claim 1 wherein $R_2$ is

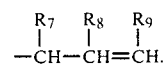

8. A steroid in accordance with claim 1 wherein $R_1$ is

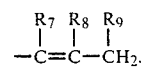

9. A steroid in accordance with claim 1 wherein $R_2$ is

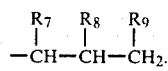

10. A steroid in accordance with claim 1 having the formula

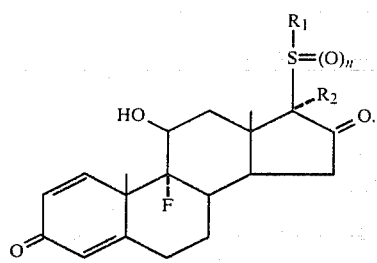

11. The steroid in accordance with claim 1, (11β,17β)-9-fluoro-11-hydroxy-17-(methylthio)-17-(2-propenyl)androsta-1,4-dien-3,16-dione.

12. A steroid having the formula

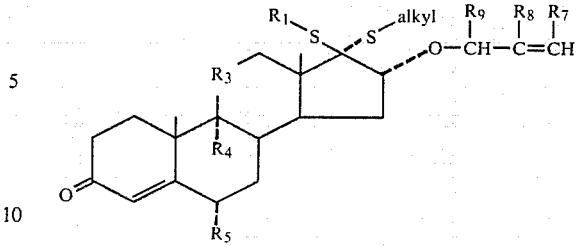

or a 1,2-dehydro derivative thereof wherein
$R_1$ is alkyl, mono-, di- or trifluoroalkyl,

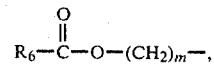

aryl or alkylthioalkyl, wherein $R_6$ is alkyl or aryl and m is 1, 2, 3 or 4;
$R_3$ is carbonyl or β-hydroxymethylene;
$R_4$ is hydrogen or halogen;
$R_5$ is hydrogen, methyl or fluorine; and
$R_7$, $R_8$ and $R_9$ are each independently hydrogen or alkyl of 1 to 4 carbon atoms.

* * * * *

UNITED STATES PATENT AND TRADEMARK OFFICE
CERTIFICATE OF CORRECTION

PATENT NO. : 4,528,138          Page 1 of 2
DATED     : July 9,1985
INVENTOR(S) : Ravi K. Varma et al.

It is certified that error appears in the above—identified patent and that said Letters Patent is hereby corrected as shown below:

In the Abstract, the first structural formula should read as follows:

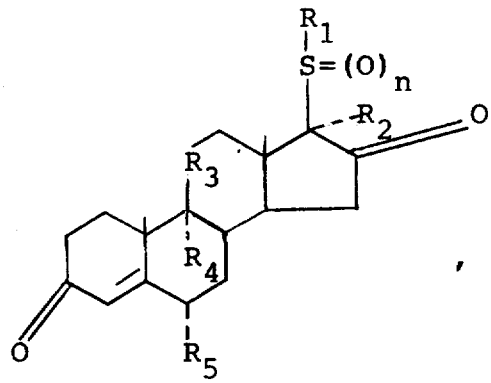

In column 6, please correct structural formula VI as follows:

UNITED STATES PATENT AND TRADEMARK OFFICE
CERTIFICATE OF CORRECTION

PATENT NO. : 4,528,138
DATED : July 9, 1985
INVENTOR(S) : Ravi K. Varma et al.

It is certified that error appears in the above-identified patent and that said Letters Patent is hereby corrected as shown below:

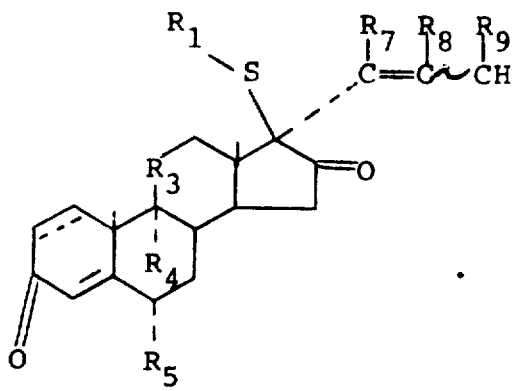

Signed and Sealed this

Third Day of December 1985

[SEAL]

Attest:

DONALD J. QUIGG

Attesting Officer     Commissioner of Patents and Trademarks